United States Patent [19]

Reimels

[11] Patent Number: 5,009,656
[45] Date of Patent: Apr. 23, 1991

[54] BIPOLAR ELECTROSURGICAL INSTRUMENT

[75] Inventor: Harry G. Reimels, Braintree, Mass.

[73] Assignee: Mentor O&O Inc., Norwell, Mass.

[21] Appl. No.: 395,264

[22] Filed: Aug. 17, 1989

[51] Int. Cl.⁵ .............................................. A61B 17/39
[52] U.S. Cl. .......................................... 606/48; 606/50
[58] Field of Search ...................... 128/303.13, 303.14, 128/303.17; 606/48, 50

[56] References Cited

U.S. PATENT DOCUMENTS

| | | | |
|---|---|---|---|
| 1,814,791 | 7/1931 | Ende | 128/303.17 |
| 3,858,586 | 1/1975 | Lessen | 128/303.17 X |
| 4,043,342 | 8/1977 | Morrison, Jr. | 128/303.14 |
| 4,476,862 | 10/1984 | Pao | 128/303.17 |
| 4,483,338 | 11/1984 | Bloom et al. | 128/303.13 |
| 4,548,207 | 10/1985 | Reimels | 128/303.17 |
| 4,593,691 | 6/1986 | Lindstrom et al. | 128/303.17 |
| 4,706,667 | 11/1987 | Roos | 128/303.14 |

Primary Examiner—Lee S. Cohen
Attorney, Agent, or Firm—Fish & Richardson

[57] ABSTRACT

A surgical instrument of the kind which is adapted to operate using bipolar energizing potential comprises a pair of adjacently disposed, elongated electrodes that receive the bipolar potential, and an electrical insulator disposed between the electrodes. The insulator terminates proximally of distal ends of the electrodes to provide a cavity across which sparking between the electrodes occurs. Thus, the instrument is useful in, e.g., arthroscopic surgery on the knee, to perform several types of procedures (such as cutting, smoothing of cartilage, and coagulation) even in the presence of an electrically conductive irrigating solution (such as saline).

30 Claims, 2 Drawing Sheets

U.S. Patent
Apr. 23, 1991
5,009,656
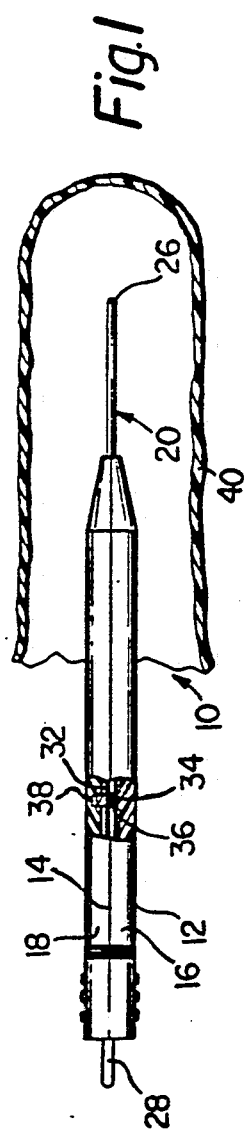
Fig.1
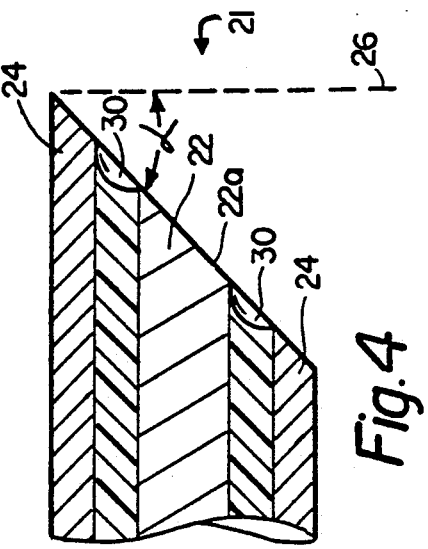
Fig.3
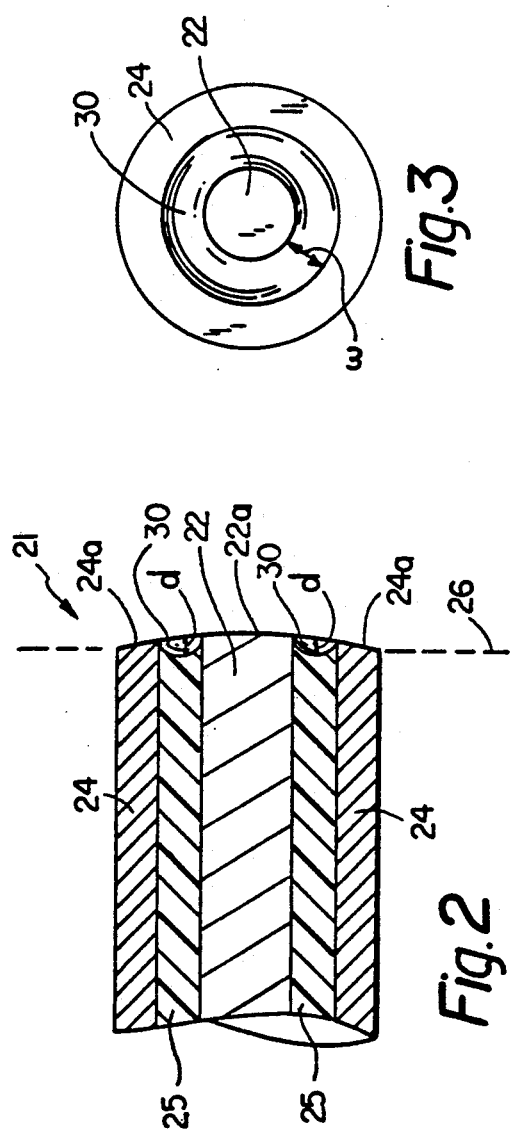
Fig.4
Fig.2

BIPOLAR ELECTROSURGICAL INSTRUMENT

BACKGROUND OF THE INVENTION

This invention relates generally to bipolar electrosurgical instruments used in arthroscopic surgery for, e.g., cutting tissue, smoothing cartilage, and coagulating bleeding vessels or tissue.

It is well known to use monopolar surgical instruments in arthroscopy for cutting, smoothing, and coagulating. A monopolar instrument includes a single electrode to which radio frequency energy is applied. The patient is securely grounded (e.g., using a ground plate) so that current flows from the tip of the electrode into the target tissue and then randomly through the patient's body to ground. To coagulate, the tip of the electrode is placed in direct contact with the bleeding vessel.

When the instrument is used for cutting, a gap is maintained by the surgeon between the electrode tip and the tissue to provide space for the generation of an electric spark necessary to produce enough heat for efficient cutting. This heat penetrates the tissue surface and creates the cut. To prevent dissipation of the high electrical energy needed to produce sparking, a nonconductive fluid such as distilled water is used in the wound in place of electrically conductive, physiologic saline solution.

Reimels, U.S. Pat. No. 4,548,207, describes a bipolar electrosurgical instrument for coagulation of blood vessels and/or tissue in the form of a probe which includes coaxial inner and outer electrodes. Radio frequency power is applied across the bipolar electrodes of the instrument, and localized coagulation is performed by placing the tip of the instrument in contact with tissue. Conductive fluids such as saline can be used with this instrument because current flows only through tissue located adjacent the electrodes.

SUMMARY OF THE INVENTION

One general aspect of the invention features a surgical instrument of the kind which is adapted to operate using bipolar energizing potential, comprising a pair of adjacently disposed, elongated electrodes adapted to receive the bipolar potential, and an electrical insulator disposed between at least a portion of the pair of electrodes and terminating proximally of distal ends of the electrodes to provide a cavity across which sparking between the distal ends occurs.

Preferred embodiments include the following features.

The electrical insulator terminates a predetermined distance proximally of the distal ends, preferably between 0.004 and 0.010 inches. The electrical insulator also spaces the distal ends apart by a predetermined amount, such as between 0.004 and 0.010 inches; most preferably, the insulator terminates 0.006 inches proximal of the distal ends and spaces the distal ends apart by 0.006 inches. The depth and width of the cavity are selected to optimize sparking.

Preferably, the pair of electrodes and the insulator are coaxial with respect to a longitudinal axis of the instrument. One of the electrodes comprises a tube disposed about at least a portion of the second electrode and is spaced therefrom by the electrical insulator, which is annular in cross-section and terminates proximally of the distal ends to form an annular cavity between them.

The electrical insulator comprises an insulating tube, that is preferably made from plastic (e.g., TEFLON ®), epoxy (e.g., high temperature epoxy), or ceramic insulating fillers. The tube is shrunk fit around the second electrode. The pair of electrodes are made of steel and their proximal ends are disposed in a housing.

In one embodiment, the distal ends of the electrodes are disposed approximately in a plane that is perpendicular to the longitudinal axis. In another embodiment, the distal ends are disposed in a plane that is beveled with respect to a plane perpendicular to the longitudinal axis. The bevel angle is between 30° and 60°. In a third embodiment, the distal ends are disposed in a plane that is parallel to the longitudinal axis.

The instrument is used to perform a surgical procedure (e.g., arthroscopy) at an operative site in the body (e.g., the knee), by inserting the surgical instrument into the operative site, applying bipolar energizing potential to the instrument to produce sparking across the cavity, and manipulating the instrument so that the sparking affects tissue at the operative site. The sparking can be used to make cuts in the tissue, or to smooth the tissue (e.g., cartilage), or to produce coagulation.

Irrigating fluid is introduced at the operative site and the sparking is produced in the presence of this fluid. Sparking occurs even when the irrigating fluid is electrically conductive (such as physiologic saline) because the sparking is localized between the distal ends of the electrodes.

The coaxial electrosurgical instrument of the invention is lightweight, small, and convenient to use. Because of the presence of the cavity between the electrode tips, the instrument efficiently produces sparking even in conductive saline solution, thus obviating the need to replace saline with non physiologic distilled water and avoiding the consequent pain that occurs prior to fluid restabilization. The localized nature of the sparking inhibits current flow through the body, thereby reducing the danger of ground plate burn or tissue damage from stray current.

Other features and advantages of the invention will be apparent from the following detailed description, and from the claims.

DESCRIPTION OF THE PREFERRED EMBODIMENTS

We first briefly describe the drawings.

FIG. 1 is a partially sectioned side view of a coaxial, bipolar electrosurgical instrument according to the present invention.

FIG. 2 is an enlarged, cross sectional view of the tip of the instrument of FIG. 1.

FIG. 3 is an end view of the tip shown in FIG. 2.

FIG. 4 is an enlarged, cross-sectional view of a tip of an alternative embodiment of the instrument of FIG. 1.

STRUCTURE AND OPERATION

Figure 5:
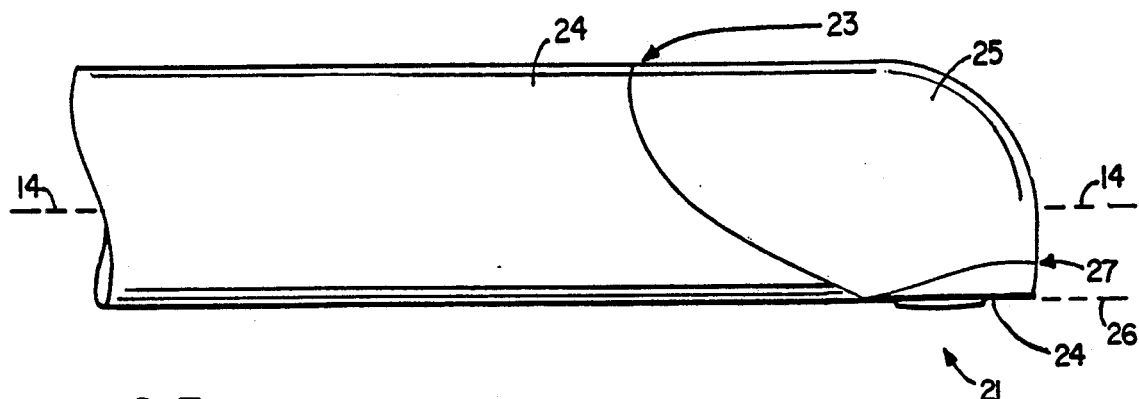
FIG. 5 is an enlarged, side-view of the tip of an alternative embodiment of the instrument of FIG. 1.

Referring to FIG. 1, a bipolar electrosurgical instrument 10 comprises a housing 12 that includes top and bottom halves 16, 1 formed of injection-molded plastic disposed along a longitudinal axis 14. Alternatively, housing 12 may be formed as a unitary structure by injection molding. Housing 12 contains a bipolar coaxial probe 20, which protrudes from the distal end of housing 12 and is also positioned along axis 14. Probe 20 has a distal end 21 having a smooth tip and/or surface that is generally disposed in a plane 26 perpendicular to axis 14.

Probe 20 includes an inner electrode 22 and an outer electrode 24 coaxially disposed about inner electrode 22 and separated therefrom by a layer 25 of electrically insulating material. A pair of contact pins 28 (only one of which is shown) are secured within the proximal end of housing 12 and are connected to respective probe electrodes 22, 24 via a pair of wires 32, 34 (e.g., 0.043 inch diameter) that run through housing 12.

The halves 16, 18 of housing 12 are held together by a snap fit between multiple protrusions 36 on portion 16 and corresponding holes 38 in the other portion 18. Additionally, either adhesive is disposed along the seam between the halves or halves 16, 18 are ultrasonically welded together. (Only one protrusion 36 and hole 38 are shown in FIG. 1.) Details of the construction of housing 12 are found in U.S. Pat. No. 4,548,207 issued to Harry G. Reimels, which is incorporated herein by reference.

Pins 28 connect to one end of a flexible cable (not shown) containing a pair of insulated leads. The other end of the cable is connected to a source (also not shown) of variable radio frequency (RF) power, as described in the aforementioned Reimels patent. After assembly, the electrosurgical instrument 10 is sterilized (e.g., by autoclaving or by exposing the instrument to ethylene oxide gas) and is then packaged for storage and/or shipment in a suitable plastic wrapper 40.

Coaxial electrodes 22, 24 are made of stainless steel, with inner electrode 22 and wire 32 constituting an integral unit. Electrically insulating layer 25, for example, a 9 inch long, 14-gauge TEFLON ® shrink tube, is placed around the distal portion of electrode 22 and heated so that it shrinks to snugly envelope the inner electrode. Then, outer electrode 24, in the form of a hollow tube, is slipped over inner electrode 22 and tube 25 and secured within housing 12 after being connected (e.g., by soldering) to wire 34, as described in the aforementioned Reimels patent.

Referring also to FIGS. 2 and 3, the tips 22a, 24a of inner and outer electrodes 22, 24, respectively, are rounded off (such as by grinding) so that the distal end 21 of probe 20 has a smooth tip and is generally disposed in plane 26. Electrically insulating layer 25 is cut back (e.g., using a hollow circular cutter) so that it terminates proximally of tips 22a, 24a to form an annular cavity 30 between electrode tips 22a, 24a. Cavity 30 serves as a "spark gap" between electrodes 22, 24, as discussed in detail below, and thus the width (w) and the depth (d) of cavity 30 are selected to optimize the efficiency of creating sparking between electrodes 22, 24 when probe 20 is inserted in the body. Applicant has found the optimum depth and width of cavity 30 to be 0.006×0.006 inches.

In use, after instrument 10 is removed from wrapper 40, it is attached to the end of the flexible cable and thus coupled to the source of variable RF power, such as that described in the aforementioned Reimels patent.

Instrument 10 is inserted into, e.g., the knee joint and the power source is activated to apply RF power to electrodes 22, 24. The surgeon selects the desired RF power setting; it is advisable to begin with a lower setting and then adjust upward as may be required. Care should be taken not to use power settings which are in excess of that needed to cut tissue, or perform cartilage smoothing or coagulation.

When sufficient power is applied across electrodes 22, 24, a series of sparks are produced between the electrodes across cavity 30. Applicant has found that the initation of the spark produces sufficient energy to dispel fluids (such as normal saline solution used to irrigate the knee joint) from between electrodes 22, 24. That is, despite the presence of electrically conductive saline at the surgical site, an air gap is essentially created within cavity 30 which more easily maintains sparking. In fact, even with tips 22a, 24a in contact with tissue, the air gap permits continuous sparking which cuts or smooths the tissue, or permits coagulation, instead of destroying the tissue. This is because current flows across the air gap rather than through the tissue (as is the case where insulation 25 is coextensive with tips 22a, 24a).

Also, when used for coagulation, the increase in the electrical impedance of the tissue as it coagulates has little or no effect on the sparking across the air gap. By contrast, in devices not including the cavity, where current flow is through the coagulating tissue, the impedance change (i.e., increase) tends to suppress the spark and inhibit cutting, smoothing, or coagulating action.

Once the tissue is sufficiently cut or smoothed, or coagulation is complete, the RF power is decoupled from instrument 10 and instrument 10 is removed from the knee joint.

Other embodiments of the invention are within the following claims.

Referring to FIG. 4, the distal end 21 of probe 20 may 7 alternatively be beveled at an angle ($\alpha$) with respect to plane 26 of between 30° and 60°. This arrangement assists the surgeon's work, as probe 20 is usually inserted into the operative site along with a microscope, the presence of which requires the surgeon to hold and manipulate probe 20 at an angle with respect to the tissue. Beveling is accomplished with any suitable technique (such as by grinding), performed before cavity 30 is formed.

Alternative geometries are also possible for distal end 21. For example, distal end 21 could be ground to a flat surface which is exactly perpendicular to longitudinal axis 14; or it can be bent to form a surface which is parallel to longitudinal axis 14.

Figure 6:
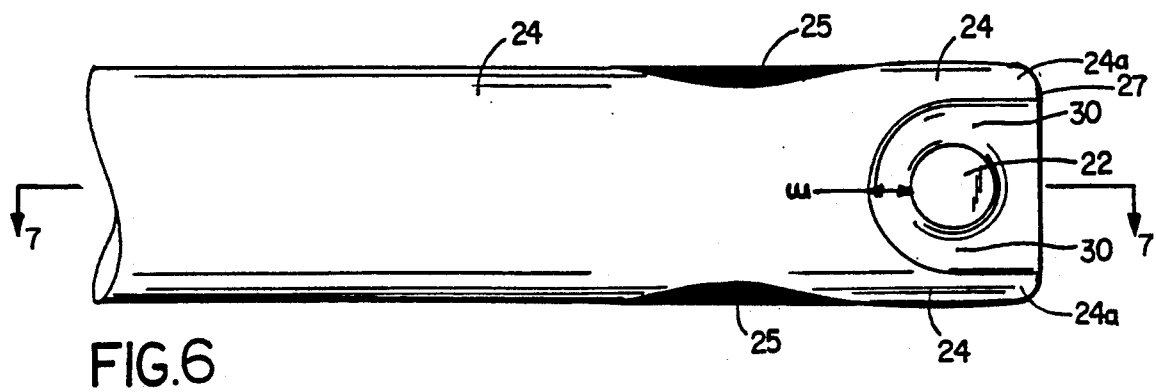
FIG. 6 is bottom-view of the tip shown in FIG. 5.
Figure 7:
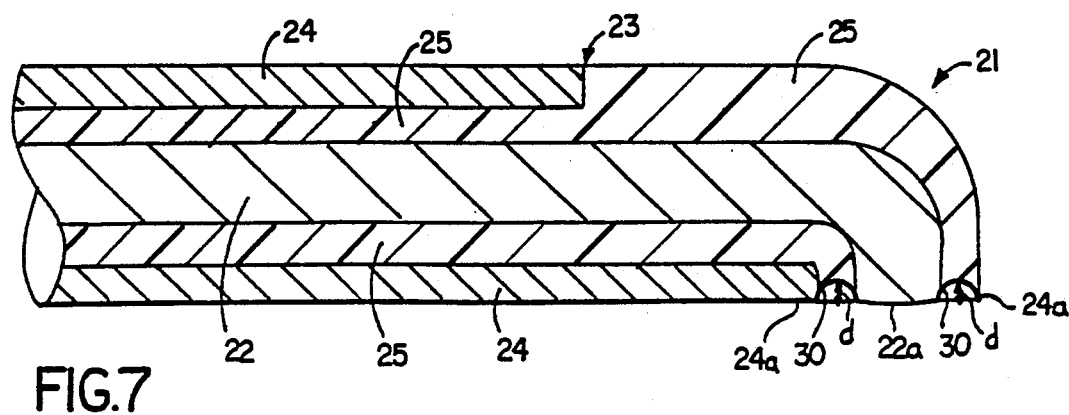
FIG. 7 is a cross sectional view taken along line 7—7 of the instrument of FIG. 6.

Referring to FIGS. 5–7, distal end 21 may alternatively be bent at 90° with respect to longitudinal axis 14 so that the plane 26 in which electrode tips 22a, 24a is disposed is parallel to longitudinal axis 14. As is the case for the embodiments of FIGS. 1–4, coaxial electrodes 22, 24 are separated by electrically insulating layer 25. In this embodiment, however, outer electrode 24, terminates proximally of distal end 21 on three sides 23, and terminates coextensively with distal end 21 on the fourth side 27.

Electrical insulating layer 25 is cut back to terminate proximally of tips 22a, 24a to form annular spark gap cavity 30 between electrode tips 22a, 24a, having a width (w) and depth (d) selected to optimize the efficiency of sparking between electrodes 22, 24. This embodiment is especially useful where manipulation of the instrument is restricted; for example, where the instrument must be inserted into the operative site of the body with longitudinal axis 14 parallel to the surface of the tissue that is to be treated.

While surgical instrument 10 has been described in the context of performing arthroscopic surgery on the knee, it is apparent that instrument 10 may be used in other types of procedures, such as eye surgery (e.g., to remove cataracts), neurosurgery, plastic surgery and general surgery. It may also be used for localized tissue destruction such as to destroy brain tumors and various cancers as a low cost substitute for laser tissue destruction. The size of the instrument may also vary for each use.

I claim:

1. A surgical instrument of the kind which is adapted to operate using bipolar energizing potential comprising
a probe having a smooth operation tip, said probe including a pair of adjacently disposed, elongated electrodes adapted to receive said bipolar energizing potential, an electrically insulating means for spacing apart and generally separating said electrodes, each said electrode also terminating at a distal end at said tip of said probe, said distal ends being generally in the same plane so that they form part of a smooth surface of said tip and so that neither distal end projects above or from said tip,
said electrically insulating means terminating proximally of said tip of said probe and of said distal ends of said electrodes to provide a cavity between said distal ends of said electrodes across which, when said instrument is in use, sparking between said distal ends of said electrodes occurs.

2. The instrument of claim 1 wherein said electrically insulating means terminates a predetermined distance proximally of said distal ends.

3. The instrument of claim 2 wherein said predetermined distance is between 0.004 and 0.010 inches.

4. The instrument of claim 3 wherein said predetermined distance is 0.006 inches.

5. The instrument of claim 1 wherein said electrically insulating means spaces the distal ends of said pair of electrodes apart by a predetermined amount.

6. The instrument of claim 5 wherein said predetermined amount is between 0.004 and 0.010 inches.

7. The instrument of claim 1 wherein said electrically insulating means terminates 0.006 inches proximally of said distal ends and spaces said distal ends apart 0.006 inches.

8. The instrument of claim 1 wherein said pair of electrodes and said insulating means are coaxial with respect to a longitudinal axis of said instrument.

9. The instrument of claim 8 wherein a first one of said electrodes comprises a tube disposed about at least a portion of a second one of said electrodes and is spaced therefrom by said electrically insulating means.

10. The instrument of claim 9 wherein said insulating means is annular in cross-section and terminates proximally of said distal ends to form an annular cavity between said distal ends of said electrodes.

11. The instrument of claim 10 wherein said electrically insulating means comprises an insulating tube that is shrunk fit around said second electrode.

12. The instrument of claim 11 wherein said tube comprises plastic.

13. The instrument of claim 12 wherein said plastic is TEFLON ®.

14. The instrument of claim 11 wherein said tube comprises epoxy.

15. The instrument of claim 11 wherein said tube comprises ceramic.

16. The instrument of claim 8 wherein the distal ends of said electrodes are disposed generally in a plane that is perpendicular to said longitudinal axis.

17. The instrument of claim 8 wherein the distal ends of said electrodes are disposed in a plane that is beveled with respect to a plane perpendicular to said longitudinal axis.

18. The instrument of claim 17 wherein said bevel is between 30° and 60°.

19. The instrument of claim 1 wherein said pair of electrodes comprises steel.

20. The instrument of claim 1 wherein the distal ends of said electrodes are disposed in a plane that is parallel to a longitudinal axis of said instrument.

21. The instrument of claim 1 wherein proximal ends of said electrodes are disposed in a housing.

22. A method of performing a surgical procedure at an operative site in the body, comprising
(a) inserting into the operative site a surgical instrument of the kind which is adapted to operate using bipolar energizing potential and which includes
a probe having a smooth operating tip, said probe including a pair of adjacently disposed, elongated electrodes adapted to receive said bipolar potential, an electrically insulating means for spacing apart and generally separating said electrodes, each said electrode also terminating a distal end at said tip of said probe, said distal ends being generally in the same plane so that they form part of a smooth surface of said tip and so that neither distal end projects above or from said tip,
said electrically insulating means terminating proximally of said tip of said probe and of said distal ends of said electrodes to provide a cavity between said distal ends of said electrodes across which, when said instrument is in use, sparking between said distal ends of said electrodes occurs;
(b) applying said bipolar energizing potential to said instrument to produce sparking across said cavity; and
(c) manipulating said instrument so that said sparking affects tissue at said operative site.

23. The method of claim 22 further comprising making cuts in said tissue using said sparking.

24. The method of claim 22 wherein at least some of said tissue is cartilage, and further comprising smoothing said cartilage using said sparking.

25. The method of claim 22 further comprising coagulating tissue using said sparking.

26. The method of claim 22 further comprising introducing irrigating fluid at said operative site and producing said sparking in the presence of said fluid.

27. The method of claim 26 wherein said fluid is electrically conductive.

28. The method of claim 26 wherein said fluid comprises saline.

29. The method of claim 22 wherein said surgical procedure is arthoscopy.

30. The method of claim 29 wherein said operative site is a region of the knee.

* * * * *